United States Patent [19]

Wideman

[11] 4,375,572
[45] Mar. 1, 1983

[54] PROCESS FOR THE CONVERSION OF TERPENES

[75] Inventor: Lawson G. Wideman, Tallmadge, Ohio

[73] Assignee: The Goodyear Tire & Rubber Company, Akron, Ohio

[21] Appl. No.: 365,695

[22] Filed: Apr. 5, 1982

[51] Int. Cl.$^3$ .................................................. C07C 5/09
[52] U.S. Cl. ................................... 585/435; 585/432; 585/440
[58] Field of Search ..................... 585/435, 440, 432

[56] References Cited

U.S. PATENT DOCUMENTS

| | | | |
|---|---|---|---|
| 2,376,308 | 5/1945 | Dixon | 585/432 |
| 2,376,310 | 5/1945 | Dixon | 585/432 |
| 2,387,836 | 10/1945 | Dixon | 585/432 |

Primary Examiner—Curtis R. Davis
Attorney, Agent, or Firm—D. O. Nickey

[57] ABSTRACT

There is disclosed a process for the conversion of terpenes to α-methyl-methylstyrenes and cymenes which comprises contacting at least one terpene, selected from the group comprised of mono- and bi-cyclic unsaturated hydrocarbons having the formula $C_{10}H_{16}$; with an alkali metal hydroxide catalyst on a support at a temperature of 300° to 500° C.

31 Claims, No Drawings

PROCESS FOR THE CONVERSION OF TERPENES

RELATED APPLICATIONS

This application is related to a patent application Ser. No. 311,220, filed Oct. 14, 1981, in the U.S. Patent and Trademark Office by the inventor herein and J. A. Kuczkowski.

TECHNICAL FIELD

This invention is concerned with the economic conversion of terpenes to α-methyl-methylstyrenes and cymenes. More specifically, this invention is concerned with a process to convert a renewable hydrocarbon source, that being the volatile oil present in trees, to a compound that can provide an alternative source of hydrocarbon feed stocks that are non-petroleum based. The process of the present invention accomplishes the conversion of terpenes to α-methyl-methylstyrenes (hereinafter DMS) by contacting at least one terpene, which is mono- or bi-cyclic unsaturated hydrocarbon having the formula $C_{10}H_{16}$; with an alkali metal hydroxide catalyst on a support at a temperature of 300° to 500° C.

BACKGROUND ART

Turpentine is the general term for the volatile oil present in trees, primarily coniferous trees. Chemically, it is predominately a mixture of unsaturated mono- and bi-cyclic $C_{10}H_{16}$ hydrocarbons. The principal component is alpha-pinene, which is present in the turpentine from all species of turpentine bearing trees.

The composition of the turpentine is determined by the species of the tree. A chromatograph of the turpentine makes a good fingerprint for identifying the species.

Although over thirty compounds have been identified in turpentine only a few have commercial significance, that is, they can be separated in high purity for subsequent use. Alpha-pinene, beta-pinene, and beta-phellandrene and dipentene are present in large enough volume in gum or sulfate turpentines of most species to make isolation feasible. Δ-3 carene is present in large quantities in certain species, especially in the northwestern and Scandinavian pines. The terpenes, as one would expect, will undergo numerous reactions including hydrogenation, isomerization, polymerization, oxidation, halogenation, esterification and dehydrogenation.

There has been and continues to this day investigations concerning the production of high volume chemicals from nonpetroleum base sources. Trees, especially, coniferous trees, are a renewable resource that can be ground into wood chips and have extracted therefrom resins and terpenes. Terpenes are therefore a renewable resource that may be used to replace the present petroleum based source of most of industry's hydrocarbons. However, a turpentine or a mixture of terpenes, in and of themselves, are not a commercially significant hydrocarbon feed stock. Therefore, a process that will readily convert a terpene or a turpentine feed stock into a valuable or commercially more acceptable compound is highly desirable.

In the past numerous publications have reported the conversion of turpentine to various chemical compounds using numerous reaction conditions and catalysts. More specifically, Mizrahi and Nigam, (*J. Chromatog.*, 25 (1966) pp. 230-241) report the dehydrogenation of seven monoterpenes to para-cymene using catalytic dehydrogenation in a reaction gas chromatograph on a micro scale. Mizrahi and Nigam disclose the use of platinum on alumina to obtain p-cymene from hydrocarbons.

The prior art also discloses the vapor phase dehydrogenation of pinene to p-cymene through the use of platinized charcoal. (*J. Chem. Soc.* (1940) pp 1139 to 1147) Further, various terpenes including limonene have been dehydrogenated to p-cymene using sulphur. See A. R. Pinder, *The Chemistry of Terpenes*, Wiley, 1960, p 43. Also, substituted α-methylstyrene has been prepared by acid catalyzed dehydration of the corresponding alcohol. (*Chemical Week*, July 30, 1980, p 25)

However, none of the prior art publications disclose or suggest the process for the conversion of terpenes to DMS which comprises contacting at least one terpene selected from the group comprised of mono- and bi-cyclic unsaturated hydrocarbons having the formula $C_{10}H_{16}$; with an alkali metal hydroxide catalyst on a support at a temperature of 300° to 500° C. at a liquid hour space velocity (LHSV) of 0.20 to 20.

DISCLOSURE OF THE INVENTION

There is disclosed a process for the conversion of terpenes to DMS which comprises contacting at least one terpene, selected from the group comprised of mono- and bi-cyclic unsaturated hydrocarbons having the formula $C_{10}H_{16}$; with an alkali metal hydroxide catalyst on a support at a temperature of 300° to 500° C.

Terpenes in the strict sense are volatile hydrocarbons of the empirical formula $C_{10}H_{16}$. In a wider sense the term includes sesquiterpenes, $C_{15}H_{24}$, diterpenes, $C_{20}H_{32}$, and higher polymers. In a still looser sense, the term includes various oxygen containing compounds derived from terpene hydrocarbons, such as alcohols, ketones and camphors. The terpenes are based on the isoprene unit, $C_5H_8$, and may be either acyclic or cyclic with one or more benzenoid groups. Representative of the terpenes that can be used in the process of the present invention are alpha-pinene, beta-pinene, limonene, Δ-3 carene, and terpinolene.

The conversion of terpenes to DMS is of significant importance since it could provide a renewable hydrocarbon source for compounds such as a replacement monomer for styrene, α-methylstyrene, phenylindane diacids and phthalic acids.

Representative of the alkali metal hydroxide catalysts that are useful in the process of this invention are sodium hydroxide, lithium hydroxide and potassium hydroxide or mixtures thereof. Preferably, sodium or potassium hydroxides are used since they are less costly. Most preferred is potassium hydroxide. The process of the present invention is conducted using the alkali metal hydroxide supported on a carrier. Supporting the alkali metal hydroxide on a carrier is required since this provides good surface area of catalyst per gram of material. Representative of the carriers upon which the alkali metal hydroxides can be supported are silica; aluminum oxide ($Al_2O_3$); magnesium oxide (MgO); carbon (C) and titanium dioxide ($TiO_2$), however, any support that does not detrimentally effect the activity of the alkali metal hydroxide and has a surface area of at least 10 $m^2/gm$ may be used.

Aluminum oxide ($Al_2O_3$) and magnesium oxide (MgO) are the preferred supports for the alkali metal hydroxides. For production of the support a great variety of modifications of aluminum oxide are suitable, such as α-, K-, H-, γ-, η- or σ- modifications; however, γ aluminum oxide is generally preferred since it is easiest in its manipulations and yields satisfactory results.

To ensure a good efficiency of the catalyst the specific surface area of the support material should generally be larger than 10 m$^2$/gm, preferably larger than 100 m$^2$/gm.

The catalyst system should contain from 2–25 percent by weight of the alkali metal hydroxide (based on the finished catalyst). At concentrations below 5 percent by weight a lower yield of DMS is realized and at concentrations above 25 percent by weight, the catalyst is more difficult to handle since it is less pourable and no advantage is realized.

Preferably, however, the catalyst contains about 5 to 15 percent by weight of alkali metal hydroxide, since high activity combined with excellent pourability is found in this range. Excellent results are obtained with the catalyst containing about 10 percent by weight of alkali metal hydroxide.

The manufacturing methods for catalysts containing alkali metals on aluminum oxide supports have been well-known to those skilled in the art for years and are disclosed in numerous popular publications and also in numerous patents, such as U.S. Pat. No. 2,836,633.

In a preferred embodiment the catalyst is produced in accordance with a very simple method by first predrying the support material for about 5 hours at a temperature of about 200°–400° C. After drying, the support material is allowed to cool to about 100° C. and then the corresponding amount of alkali metal hydroxide is added in a mechanical mixing device under a protective gas atmosphere. At the temperature employed the metal hydroxide uniformly distributes itself on a support material. In addition, the alkali metal hydroxide may be dispersed upon the carrier as an aqueous solution. If desired, the catalyst can further be subjected to high temperatures after treatment, by heating the same for about 2 to 20 hours at 200°–600° C. in air or an inert atmosphere i.e. nitrogen.

After its manufacture the catalyst may be in the form of powder, granules, pellets or extrudates.

The temperature which the process of the present invention can be conducted ranges from 300° to 500° C. A more preferred temperature range is from 350° to 480° C. with the most preferred being 400° to 475° C.

The process of the present invention is conducted in a continuous manner, however, the concept may be altered to encompass a batch process. However, numerous operating difficulties and poor yields may result from the operation of the present invention in a batch or a semi-continuous nature. The process of the present invention is carried out in the vapor phase since the reaction temperature is greater than that of the boiling point of the starting materials.

The amount of catalyst employed is related to the LHSV of the reaction system. The LHSV should be large enough, above 0.20 so as to effect efficient conversion of terpenes to DMS. A LHSV of 0.4 to 10 is particularly advantageous. Within this ratio the reaction can be controlled to give high yields of DMS.

A liquid hourly space velocity ratio or throughout of material through the reactor that is suitable for the process of the present invention is 0.20 to 20. Liquid hour space velocity, hereinafter known as LHSV, is meant to mean a volume of liquid throughput per gross volume of catalyst. A gross volume of catalyst is the actual volume plus the interstitial volume. For example, 90 ml of liquid feed stock is passed over 45 cc (gross volume) of catalyst in one hour to yield an LHSV of 2. See *Chem. Eng. Kinetics*, J. M. Smith, McGraw-Hill, N.Y., pp 99–100 (1956).

BEST MODE FOR CARRYING OUT THE INVENTION

The process of the present invention is generally carried out in a tubular reactor in an upflow or downflow manner. A preheater is used to vaporize the terpenes prior to passage through the reactor. The reaction can be carried out at atmospheric pressure, super- and subatmospheric pressure, there being no appreciable economic advantage to either. Proper temperature control of the catalyst bed and reaction wall temperatures is rerequired to achieve satisfactory results. A flow of an inert gas, for example, nitrogen or carbon dioxide, is used as the carrier gas in the reactor. The reactor catalyst bed and the preheater are all brought up to the reaction temperature prior to introduction of the terpene stream. The terpene feed stream is volatilized in the preheater and then is carried by the inert gas to the reactor which contains the catalyst bed. This rate of flow of material over the catalyst bed may range from 0.20 to 20 with a rate of 0.4 to 20 being more preferred and a rate of 0.4 to 10 being the most preferred.

The advantages obtainable by means of the present invention reside in that the aforementioned terpenes can be converted with high selectivity into DMS with a relatively inexpensive catalyst and within short reaction periods.

PREPARATION OF THE CATALYST

A commercially available aluminum oxide having a surface area of 80–234 m$^2$/gm and consisting of 98 percent by weight of $Al_2O_3$ wherein 95 percent is in the gamma form and 5 percent is in the alpha form should be dried at elevated temperatures under nitrogen in a container equipped with an agitator. The aluminum oxide is then allowed to cool to about 100° C. and a stoichiometric amount of the alkali metal hydroxide which is dissolved in water is added thereto. The alkali metal hydroxide in this case, specifically, potassium hydroxide is distributed on the support by agitation. During the agitating step the temperature is held at about 100° C. The catalyst is then heated in air or an inert atmosphere to dry the prepared catalyst.

EXAMPLE 1

Conversion of Turpentine to DMS with 10% KOH/$Al_2O_3$

A 10 inch by three-quarter inch stainless steel reactor was charged with 45 cc of 10 percent KOH/$Al_2O_3$ as the catalyst and flushed with a constant flow of 7 ml per minute of nitrogen. A typical turpentine feed (wt.%) consists of 54 percent was α-pinene, 38 percent β-pinene, 5 percent limonene, 1–2 percent p-menthane isomers (cis and trans), 1–2 percent terpinolene, 1–2 percent terpinene, 1–2 percent menthadienes and 1–2 percent Δ-3 carene. Turpentine was metered into the tubular reactor in a downflow manner. The turpentine contained 10 percent heptane as an internal gas chromatograph standard. A glass bead preheater was used to vaporize the feed prior to contact with the catalyst. Nitrogen as a carrier gas at 7 ml/min. was metered into the reactor concurrently with the turpentine stream. The reactor contained a heating jacket with manual temperature controls and a catalyst bed thermocouple array to monitor the internal temperature. The reactions were carried out at atmospheric pressure.

The tubular reactor and preheater were heated to the desired reaction temperature before introduction of the feed. The effluent stream from the reactor was condensed in a dry ice acetone bath prior to gas chromatograph and NMR analysis. The sensitivity of turpentine and DMS to the GC detector had been predetermined. The samples were collected after one hour on stream. The percent of product distribution for the runs is presented in Table 1.

TABLE I

CONVERSION OF TURPENTINE WITH 10% KOH/Al$_2$O$_3$

| Catalyst | Reaction Temp. | LHSV | % Yield | | | |
|---|---|---|---|---|---|---|
| | | | p-cymene | o-cymene | DMS | p-menthane |
| 10% KOH/Al$_2$O$_3$ 234 m$^2$/gm, dried at 400° C. under nitrogen | 450° C. | 0.48 | 30 | 11 | 33 | <1 |

To illustrate this fact cymenes were passed over the same catalyst.

EXAMPLE II

Conversion of Cymenes to DMS

The catalyst and the reactor were as described in Example I, however, feed stock, loading of the catalyst, temperature of reaction, LHSV of the reaction, drying of the catalyst, and surface area of the catalyst were varied. The parameters and the resulting data are set out in Table II.

TABLE II

CONVERSION OF CYMENES TO DMS

| RUN # | CATALYST | CYMENE FEED | REACTION TEMP. | LHSV | % CONVERSION | DMS % SELECTIVITY |
|---|---|---|---|---|---|---|
| (1) | 10% KOH/Al$_2$O$_3$ 234 m$^2$/gm- dried at 600° C. in air | p-cymene | 400° C. | 0.48 | 7 | 93 |
| (2) | Cat from #1 | Mixed 33% para 62% meta 5% ortho | 400° C. | 0.48 | 5 | 91 |
| (3) | 10% KOH/Al$_2$O$_3$ 234 m$^2$/gm dried at 400° C. in N$_2$ | Mixed as in #2 | 450° | 0.48 | 46 | 85 |
| (4) | Cat from #3 | p-cymene | 450° C. | 0.48 | 51 | 83 |
| (5) | 10% NaOH/Al$_2$O$_3$ 234 m$^2$/gm dried at 400° C. in N$_2$ | p-cymene | 450° C. | 0.48 | 7 | 78 |
| (6) | 10% KOH/Al$_2$O$_3$ 4 m$^2$/gm dried at 400° C. in N$_2$ | p-cymene | 450° C. | 0.48 | 8 | 64 |
| (7) | 5% KOH/Al$_2$O$_3$ 234 m$^2$/gm dried at 400° C. in N$_2$ | p-cymene | 450° C. | 0.48 | 10 | 74 |
| (8) | 20% KOH/Al$_2$O$_3$ 234 m$^2$/gm dried at 400° C. in N$_2$ | p-cymene | 450° C. | 0.48 | 28 | 98 |
| (9) | Cat from #3 | p-cymene | 350° | 0.24 | 24 | 98 |
| (10) | Cat from #3 | p-cymene | 375° C. | 0.24 | 31 | 98 |
| (11) | Cat from #3 | p-cymene | 400° C. | 0.24 | 36 | 93 |
| (12) | Cat from #3 | p-cymene | 425° C. | 0.24 | 47 | 75 |
| (13) | Cat from #3 | p-cymene | 450° C. | 0.24 | 54 | 70 |
| (14) | Cat from #3 | p-cymene | 350° C. | 0.48 | 23 | 90 |
| (15) | Cat from #3 | p-cymene | 400° C. | 0.48 | 40 | 77 |
| (16) | Cat from #3 | p-cymene | 475° C. | 0.48 | 59 | 57 |

The results indicate that an alkali metal hydroxide can effectively and efficiently dehydrogenate and aromatize the feed stock to the more valuable aromatic compounds. Although the yield of para and ortho cymene was greater than the highly desired DMS, it should be apparent to those skilled in the art that the para and ortho cymenes would be recycled back to the reactor for further conversion of DMS. The ease of separation of cymenes from DMS allows a high ultimate yield of DMS.

From Table II it is evident that the catalysts and process of the present invention will readily convert p-cymene to DMS. Run #3 and 4 set out the most preferred catalyst, catalyst preparation and reaction conditions.

EXAMPLE III

Comparative Example

An unloaded catalyst support (Al$_2$O$_3$ with a surface area of 234 m$^2$/gm) and a commercially accepted dehydrogenation catalyst (palladium on alumina) were evaluated as described in Example I.

TABLE III
COMPARATIVE DATA

| Run # | Catalyst | Feed | Reaction Temp. | LHSV | Cymene Conversion % | D.M.S. Sel. % |
|---|---|---|---|---|---|---|
| 1 | $Al_2O_3$-234 $m^2$/gm dried at 400° C. in $N_2$ | p-cymene | 450 | 0.48 | 54 | 4 |
| 2 | 0.3% Pd/$Al_2O_3$ dried at 400° C. in $N_2$-234 $m^2$/gm | p-cymene | 350 | 0.48 | 22 | 54 |
| 3 | From Run #2 | p-cymene | 375 | 0.48 | 29 | 42 |
| 4 | From Run #2 | p-cymene | 400 | 0.48 | 46 | 17 |
| 5 | From Run #2 | p-cymene | 425 | 0.48 | 58 | 10 |
| 6 | From Run #2 | p-cymene | 450 | 0.48 | 69 | 8 |
| 7 | From Run #2 | p-cymene | 475 | 0.48 | 76 | 6 |
| 8 | $Al_2O_3$-234 $m^2$/gm | Dipentene 122* | 450 | 0.48 | 23 (% yield) | 8 plus 15% p-menthane (% yield) |

*Dipentene 122 is a commercial terpene fraction from Hercules Incorporated which is described in greater detail infra.

The comparative examples demonstrate that the alkali metal hydroxide catalysts provide an efficient and effective means to convert terpenes to the more desired aromatics.

At present, commercial terpene streams are available which consist of the turpentine feedstock which has had the more valuable components removed therefrom. Three such terpene streams are Solvenol 2, Solvenol 3 and Dipentene 122 from Hercules Incorporated of Wilmington, Del., U.S.A.

The following analysis of the commercially available terpene streams was done by gas chromotography using area normalization. These particular results were obtained using 25% carbowax 1,000 on 80-100 mesh chromosorb WHP in a $\frac{1}{8}"\times 15$ foot nickel column with 60 cc/min He. The injection port and flame ionization detector were at 250° C. The sample size was 0.5 microliter and the temperature was programmed from 80°-200° C. at 2° C./min.

ANALYSIS OF COMMERCIALLY AVAILABLE TERPENE STREAMS

|  | Solvenol 2 (S-2) | Solvenol 3 (S-3) | Dipentene 122 (D-122) |
|---|---|---|---|
| α-pinene/p-menthane | 5.6 | 15.4 | 4.9 |
| unknown | 1.1 | 1.3 | — |
| Camphene | 6.0 | 1.0 | 0.5 |
| β-pinene | 6.1 | 1.5 | 0.4 |
| carvomenthene | 0.9 | 4.4 | 2.5 |
| 3-carene/myrcene | 3.0 | 0.4 | — |
| α-phellandrene | 4.6 | 1.8 | 0.6 |
| α-terpinene | 4.9 | 5.2 | 2.6 |
| dipentene | 43.1 | 47.5 | 26.8 |
| β-phellandrene | 1.9 | — | — |
| γ-terpinene | 2.1 | 1.3 | 3.2 |
| p-cymene | 4.6 | 16.3 | 7.9 |
| terpinolene | 10.00 | 3.1 | 45.1 |
| unknown | 0.3 | 0.1 | 0.1 |
| unknown | 0.6 | — | 0.1 |
| unknown | 0.6 | — | 0.1 |
| fenchone | 0.5 | 0.6 | 2.4 |
| α, p-dimethyl styrene | 0.5 | 0.1 | 1.5 |
| unknown | 0.2 | — | — |
| camphor | 0.8 | — | — |
| alcohols | 2.5 | — | 0.7 |
| Total | 99.9 | 100.0 | 99.4 |

EXAMPLE IV

Process of the Present Invention Used to Convert Commercial Terpene Streams

The reactor and reaction conditions as set out in Example 1 were used. Table IV contains the pertinent data.

The following examples are presented to demonstrate that the process of the present invention can efficiently convert commercially available terpene streams to more valuable feedstocks.

TABLE IV

| Run # | Catalyst Reactor Pressure | feed | Reaction Temp. | LHSV | % Yield p-cymene | o-cymene | DMS | p-methane |
|---|---|---|---|---|---|---|---|---|
| 1 | 10% KOH/$Al_2O_3$ 234 $m^2$/gm dried at 600° C. | Dipentene 122 (D-122) | 450 | 0.48 | 60 | — | 15 | 14 |
| 2 | Cat from Run #1 | D-122 | 400 | 0.48 | 70 | 1 | 6 | 8 |
| 3 | 10% KOH/$Al_2O_3$ | D-122 | 400 | 0.48 | 71 | — | 5 | 18 |

TABLE IV-continued

| Run # | Catalyst Reactor Pressure | feed | Reaction Temp. | LHSV | % Yield p-cymene | o-cymene | DMS | p-methane |
|---|---|---|---|---|---|---|---|---|
| 4 | 234 m²/gm dried at 400° C. in N₂ Cat from Run #3 Reactor pressure atmospheric minus 50 mm Hg. | limonene technical grade | 450 | 0.48 | 48 | — | 34 | 10 |
| 5 | Cat from #3 reactor pressure atmospheric minus 200 mm of Hg | D-122 | 450° C. | 0.48 | 59 | — | 13 | 15 |
| 6 | Cat from Run #3-atmospheric pressure | D-122 | 450° C. | 0.48 | 49 | — | 30 | 13 |
| 7 | Cat from Run #3 | D-122 | 450° C. | 3.0 | 54 | — | 26 | 13 |
| 8 | Cat from Run #3 | Limonene | 450° C. | 0.48 | 59 | — | 34 | — |
| 9 | Cat from #3 | Limonene | 475° C. | 0.48 | 47 | — | 46 | — |
| 10 | 10% NaOH/Al₂O₃ 234 m²/gm dried at 400° C. in N₂ | Limonene | 450 | 0.48 | 90 | — | 5 | — |
| 11 | 10% KOH/Al₂O₃ 4 m²/gm dried at 400° C. in N₂ | D-122 | 450 | 0.48 | 63 | — | 11 | 16 |
| 12 | 5% KOH/Al₂O₃ 234 m²/gm dried at 400° C. in N₂ | Limonene | 450° C. | 0.48 | 91 | — | 5 | — |
| 13 | 20% KOH/Al₂O₃ 234 m²/gm dried at 400° C. in N₂ | Limonene | 450 | 0.48 | 83 | — | 13 | — |
| 14 | 10% KOH/MgO 17 m²/gm dried at 400° C. in N₂ | Limonene | 450 | 0.48 | 58 | — | 36 | — |
| 15 | Cat from Run #14 | D-122 | 450 | 0.48 | 41 | 1 | 31 | 12 |
| 16 | Cat from Run #3 | S-3 | 300 | 0.48 | 54 | — | 1 | 33 |
| 17 | Cat from #3 | D-122 | 300 | 0.48 | 49 | — | 2 | 27 |
| 18 | Cat from #3 | S-2 | 350 | 0.48 | 58 | 5 | 4 | 14 |
| 19 | Cat from #3 | S-3 | 350 | 0.48 | 57 | 1 | 6 | 29 |
| 20 | Cat from #3 | D-122 | 350 | 0.48 | 64 | — | 7 | 20 |
| 21 | Cat from #3 | S-2 | 400 | 0.48 | 50 | 6 | 19 | 8 |
| 22 | Cat from #3 | S-3 | 400 | 0.48 | 47 | 2 | 22 | 22 |
| 23 | Cat from #3 | D-122 | 400 | 0.48 | 53 | 3 | 25 | 11 |
| 24 | Cat from #3 | S-2 | 450 | 0.48 | 41 | 4 | 28 | 7 |
| 25 | Cat from #3 | S-3 | 450 | 0.48 | 35 | 2 | 26 | 18 |
| 26 | Cat from #3 | D-122 | 450 | 0.48 | 40 | 3 | 32 | 6 |

This data indicates that the process of the present invention operates under numerous and varied conditions. Depending upon the feed stock the yield of DMS varied from 5% to 46%. Runs 10, 12 and 13 point out the conditions that are favorable for cymene production, however, if DMS is desired a preferred embodiment is found in Run #9.

APPLICABILITY OF DMS

Dimethyl styrene, especially the para isomer can be an important monomer in the rubber industry raw material portfolio. DMS may be a partial or perhaps total replacement monomer for styrene. DMS may also be used as an intermediate in a process for making p-phenylindane diacid for high glass transition temperature polyester.

Samples of DMS made by the process of the present invention have been evaluated as monomers in block and emulsion polymerization process. It has been determined that a polymer prepared with the proper ratio of DMS to butadiene can be made that matches the Tg (glass transition temperature) of any desired SBR. Since Tg's are a fundamental property relating to the rubberiness of a polymer, one skilled in this art would readily conclude that DMS is a viable replacement for styrene.

Industrial Applicability

The process of the present invention provides a means for the conversion of a renewable feed stock, that being turpentine, to aromatic compounds that are significantly more important as a commercial feed stock. In addition, the process of the present invention accomplishes this conversion without the use of expensive and sometimes easily poisoned catalysts, such as platinum on carbon, and does so in an efficient and selective manner. Thus, the process of the present invention provides a viable and economic means for the conversion of a renewable hydrocarbon feed stock into a more commercially acceptable aromatic feed stock.

While certain representative embodiments and details have been shown for the purpose of illustrating the invention, it will be apparent to those skilled in this art that various changes and modifications may be made therein without departing from the scope of the invention.

I claim:

1. A process for the conversion of terpenes to α-methyl-methylstyrenes which comprises contacting at least one terpene selected from the group comprised of mono- and bi-cyclic unsaturated hydrocarbons having the formula $C_{10}H_{16}$, with an alkali metal hydroxide catalyst on a support at a temperature of 300° to 500° C.

2. A process according to claim 1 wherein the terpenes are selected from the group consisting of α-pinene, β-pinene, limonene, p-menthane, (cis and trans isomers) terpinolene, terpinene, menthadiene and Δ-3 carene.

3. A process according to claim 1 wherein the alkali metal hydroxide is selected from the group consisting of NaOH and KOH.

4. A process according to claim 1 wherein the alkali metal hydroxide catalyst is supported on a carrier selected from the group consisting of silica, aluminum oxide, magnesium oxide, carbon and titanium dioxide.

5. A process according to claim 1 wherein the temperature of the reaction is from 350° to 450° C.

6. A process according to claim 1 wherein the temperature is from 380° to 425° C.

7. A process according to claim 1 wherein the alkali metal hydroxide is potassium hydroxide and the support is $Al_2O_3$.

8. A process according to claim 1 wherein the alkali metal hydroxide is KOH and the support is magnesium oxide.

9. A process for the conversion of terpenes to α-methyl-methylstyrenes which comprises contacting at least one terpene selected from the group comprised of mono- and bi-cyclic unsaturated hydrocarbons having the formula $C_{10}H_{16}$, with an alkali metal hydroxide catalyst on a support that has a surface area of at least 10 m²/gm, at a temperature of 300° to 475° C.

10. A process according to claim 9 wherein the terpenes are selected from the group consisting of α-pinene, β-pinene, limonene, p-menthane, (cis and trans isomers) terpinolene, terpinene, menthadiene and Δ-3 carene.

11. A process according to claim 9 wherein the alkali metal hydroxide is selected from the group consisting of NaOH, LiOH and KOH.

12. A process according to claim 9 wherein the alkali metal hydroxide catalyst is supported on a carrier selected from the group consisting of silica, aluminum oxide, magnesium oxide, carbon and titanium dioxide.

13. A process according to claim 9 wherein the temperature of the reaction is from 350° to 450° C.

14. A process according to claim 9 wherein the temperature is from 380° to 425° C.

15. A process according to claim 9 wherein the alkali metal hydroxide is NaOH and the support is titanium dioxide.

16. A process according to claim 9 wherein the alkali metal hydroxide is KOH and the support is $Al_2O_3$.

17. A process for the conversion of terpenes to α-methyl-methylstyrenes which comprises contacting at least one terpene selected from the group comprised of mono- and bi-cyclic unsaturated hydrocarbons having the formula $C_{10}H_{16}$, with an alkali metal hydroxide catalyst on a support, at a temperature of 300° to 500° C., at a liquid hour space velocity (LHSV) of 0.20 to 20.

18. A process according to claim 17 wherein the terpenes are selected from the group consisting of α-pinene, β-pinene, limonene, p-menthane, (cis and trans isomers) terpinolene, terpinene, menthadiene and Δ-3 carene.

19. A process according to claim 17 wherein the alkali metal hydroxide is selected from the group consisting of NaOH, LiOH and KOH.

20. A process according to claim 17 wherein the alkali metal hydroxide catalyst is supported on a carrier selected from the group consisting of silica, aluminum oxide, magnesium oxide, carbon and titanium dioxide.

21. A process according to claim 17 wherein the temperature is from 350° to 450° C.

22. A process according to claim 17 wherein the temperature is from 380° to 425° C.

23. A process according to claim 17 wherein the alkali metal hydroxide is sodium hydroxide and the support is titanium dioxide.

24. A process according to claim 17 wherein the alkali metal hydroxide is KOH and the support is $Al_2O_3$.

25. A process according to claim 17 wherein the LHSV is from 0.25 to 15.

26. A process according to claim 17 wherein the LHSV is from 0.3 to 10.

27. A process according to claim 17 wherein the LHSV is from 0.4 to 10.

28. A process for the conversion of terpenes to α-methyl-methylstyrenes which comprises contactat least one terpene selected from the group comprised of mono- and bi-cyclic unsaturated hydrocarbons having the formula $C_{10}H_{16}$, with KOH on an aluminum oxide carrier at a temperature of 400° to 475° C. at a LHSV of 0.4 to 10.

29. A process for the conversion of terpenes to α-methyl-methylstyrenes which comprises contacting at least one terpene selected from the group comprised of mono- and bi-cyclic unsaturated hydrocarbons having the formula $C_{10}H_{16}$ with KOH on an aluminum oxide carrier at a temperature of 400° to 450° C. at a LHSV of 0.4 to 10.

30. A process for the conversion of terpenes to α-methyl-methylstyrenes which comprises contacting at least one terpene selected from the group comprised of mono- and bi-cyclic unsaturated hydrocarbons having the formula $C_{10}H_{16}$, with NaOH on a magnesium oxide carrier at a temperature of 400° to 450° C. at a LHSV of 0.4 to 10.

31. A process for the conversion of terpenes which comprises contacting at least one terpene selected from the group comprised of mono- and bi-cyclic unsaturated hydrocarbons having the formula, $C_{10}H_{16}$, with an alkali metal hydroxide selected from the group of NaOH, and KOH, on an inert support with a surface area of at least 10 $m^2/gm$, at a temperature of 400° to 475° C. and at a LHSV of 0.4 to 10.

* * * * *